United States Patent [19]

Cowan et al.

[11] Patent Number: 5,041,371
[45] Date of Patent: Aug. 20, 1991

[54] GENETIC MARKER FOR SUPERIOR MILK PRODUCTS IN DAIRY CATTLE

[75] Inventors: Charles M. Cowan, Waunakee; Margaret R. Dentine, Madison; Roy L. Ax, Middleton; Linda A. Schuler, Madison, all of Wis.

[73] Assignee: Wisconsin Alumni Research Foundation, Madison, Wis.

[21] Appl. No.: 324,278

[22] Filed: Mar. 15, 1989

[51] Int. Cl.[5] .................... C12Q 1/68; C12N 1/20; C12P 19/34
[52] U.S. Cl. .......................... 435/6; 435/91; 935/78
[58] Field of Search ............ 435/6, 253, 91, 243; 935/78

[56] References Cited

U.S. PATENT DOCUMENTS

| | | | |
|---|---|---|---|
| 4,495,280 | 1/1985 | Bujard et al. | 435/6 |
| 4,666,839 | 5/1987 | Souza | 435/91 |
| 4,675,297 | 6/1987 | Baxter et al. | 435/253 |
| 4,725,549 | 2/1988 | Cooke et al. | 435/243 |
| 4,767,711 | 8/1988 | Schuler et al. | 435/243 |

OTHER PUBLICATIONS

Miller et al. (1981), Cloning of Bovine Production cDNA and Evolutionary Implications of its Sequence, DNA 1 (1) 37-50.
J. Beckmann et al., 17 Animal Genetics, 25-38 (1986).
S. Camper et al., 3 DNA 237-249 (1984).
E. Hallerman et al., 18 Animal Genetics, 213-222 (1987).
W. Miller, 1 DNA, 313-314 (1982).
J. Beckmann et al., 67 Theoretical and Applied Genetics, 35-43 (1983).
D. Botstein et al., 32 Am. J. Hum. Genet. 314-331 (1980).
H. Kazazian, 31 Clin. Chem. 1509-1513 (1985).
D. Borenfreund et al., 191 Nature, 1375-1377 (1961).
P. Rigby et al., 113 J. Mol. Biol., 237-251 (1977).
C. Sapienza et al., 328 Nature, 251-254 (1987).
E. Southern, 98 J. Mol. Biol., 503-517 (1975).
N. Sasavage et al., 257 J. Biol. Chem., 678-681 (1982).
I. Hoeschele, 76 Theor. Appl. Genet., 311-319 (1988).
I. Hoeschele, 76 Theor. Appl. Genet., 81-92 (1988).
P. Stam, The Use of Marker Loci in Selection for Quantitative Characters in Exploiting New Technologies in Animal Breeding, Genetic Developments, pp. 170-182 (1986).
C. Smith et al., 103 J. Anim. Breedg. Genet., 205-217 (1986).
M. Soller et al., Genomic Genetics and the Utilization for Breeding Purposes of Genetic Variation Between Populations, pp. 161-188 in Proceedings of the Second International Conference on Quantitative Genetics, Sinauer Associates, Publishers (1988).
Miller et al., Endocrinology, 107(3) 851-54 (1980).
Miller W., Pediatric Res., 14 (4 part 2), 481 (1980)b.
Schuller et al., P.N.A.S., 84(16) 5650-54 (1987).
Theilman et al., Animal Genet. 20(3), 157-66 (1989).
Ebbitt et al., DNA 8(3):161-70 (1989).
Cowan et al., Animal Genet 20:157-65 (1989).

Primary Examiner—Robert A. Wax
Assistant Examiner—Miguel Escallon
Attorney, Agent, or Firm—Quarles & Brady

[57] ABSTRACT

An assay for a genetic marker associated with increased milk production is disclosed. Also disclosed are kits for use in connection with the assay and breeding methods that use the assay. The assay centers on finding a genetic marker in a bovine cell (e.g. in the DNA of the cell). The presence of the marker is confirmed by exposing a gene sequence from the cell to a restriction enzyme so as to yield gene fragments of varying lengths. During a separation step there is a separation of some of the fragments from others (such as by using electrophoresis), and there is then a hybridization of a plurality of probes that contain a portion of bovine prolactin sequence to the separated fragments. The probe is radiolabelled. Then, there is a comparison of the results of the hybridization with the hybridization results for a gene sequence known to either have the marker or not have the marker. The assay appears to be of greatest utility in connection with the Carlin-M Ivanhoe Bell Holstein family.

12 Claims, 1 Drawing Sheet

GENETIC MARKER FOR SUPERIOR MILK PRODUCTS IN DAIRY CATTLE

This invention was made with government support under National Science Foundation (NSF) Grant No. DCM8608739. The U.S. Government has certain rights to this invention.

BACKGROUND OF THE INVENTION

A. Field Of The Invention

The present invention relates to recombinant DNA technology. More specifically it relates to a means of determining from restriction fragment hybridization patterns whether a gene polymorphism associated with improved milk production is present in a bovine cell.

B. Description Of The Art

With the competitive pressures that the dairy industry is facing, there has been significant interest in breeding and selecting dairy cattle which have improved milk production characteristics. Significant improvements have been achieved using standard breeding techniques in which progeny are studied. Their production results are then used to guide further breeding. One particularly successful family (from a milk production standpoint) is the Holstein line deriving from Carlin-M Ivanhoe Bell (registration number 1667366, Holstein-Friesian Association, Brattleboro, Vt.). It has been estimated that currently more than 25% of the highest total performance index Holstein bulls in the U.S. are progeny of this individual.

Unfortunately, such standard techniques require years to evaluate the true genetic value by progeny testing each bull. During progeny testing, many cows must be bred and give birth to offspring. The females must be raised, bred, allowed to give birth and, finally milked for a minimum length of time. The costs of confirming that a particular bull has superior genetics is therefore very high.

Given the problems involved in using standard selection techniques, some have tried to improve milk production by locating genes that express proteins important to milk production, cloning them, and then adding commercially produced amounts of these proteins to feeds, drugs, and the like. Various bovine genes have in fact been shown to express proteins that are important for the control of mammary growth, lactogenesis, and/or lactation. One of these, bovine prolactin, is approximately 10 kilobases (kb) in length. See S. Camper et al., 3 DNA 237-249 (1984). Unfortunately, there has been significant political and regulatory resistance to the introduction of such methods.

Various other research has discovered that polymorphisms (change in the genetic code) can be associated with recognizable differences in restriction fragment lengths of certain portions of the human genome. This has been of value in creating an assay for certain genetic diseases in humans. See e.g. D. Botstein et al., 32 Am. J. Human Gene. 314-331 (1980).

Polymorphisms which do not affect amino acid composition have been reported adjacent to the bovine prolactin gene. These bovine prolactin studies have generally focused on differences around these loci between breeds or among individuals of an undetermined relationship. To date, applicants are unaware of anyone else having successfully located any polymorphism associated with a bovine gene which is indicative of improved milk production.

Thus, it can be seen that a need exists for a means of more efficiently selecting and breeding cattle for the trait of improved milk production.

SUMMARY OF THE INVENTION

In one embodiment, there is provided an assay for the presence in a bovine gene sequence of a genetic marker that is located within 1.5 kb of a bovine prolactin coding exon in the sequence. The marker is indicative of an inheritable trait of increased milk production in progeny.

The assay involves exposing the gene sequence to a restriction enzyme (e.g. Ava II) so as to yield gene fragments of varying lengths; then separating at least some of the fragments from others (e.g. using electrophoresis); then hybridizing a plurality of probes (e.g. radio-labelled cDNA probes) that contain a portion of a bovine prolactin gene sequence to the separated fragments; and then comparing the results of the hybridization with assay results for a bovine gene sequence known to have the marker or a bovine gene sequence known not to have the marker. The preferred bovine gene sequence is from a Holstein Carlin-M Ivanhoe Bell cell or its progeny.

In another embodiment, the invention provides a kit for assaying for the presence in a bovine gene sequence of a genetic marker that is located within 1.5 kb of a bovine prolactin coding exon in the sequence, the marker being indicative of an inheritable trait of increased milk production in progeny. The kit has a probe containing a portion of a bovine prolactin gene sequence, and also a bovine gene sequence known to contain said marker. The probe is preferably a cDNA sequence of a portion of bovine prolactin and the probe can be radio-labelled.

The gene sequence containing the marker is preferably a sequence contained in the cell of ATCC 40573, or its progeny, or sequences derived from either. The kit may also contain a restriction enzyme such as Ava II.

In another embodiment there is a breeding method whereby one conducts an assay of the above type on a plurality of gene sequences from different bovine cells to be selected from, and one then drops out of the breeding program at least one of the cells (or its progeny) that do not contain the marker.

It will be appreciated that the present invention can reduce the number of animals selected to achieve the same goal and reduce breeding costs:

1. Young bull calves can be tested before entry into sire programs. Those without the marker would be selected not to be continued in the program.

2. Daughters of bulls in this family who are being considered as mates could be tested. Those that are of an especially elite type AA (as described below) could be selected as preferable because they increase the chances for the elite marker being passed along.

3. When the line goes to the commercial stage, daughters could be tested at birth. Those not having the marker could be culled, and those having it could be used for milk production.

4. The screening process could be used to lower the number of bulls needed to be tested to maintain the same selection advantages as exist today.

It should be appreciated that the marker gene provides information as a supplement to other traditional tools for selection. However, in cases of equal pedigree merit, the marker will help distinguish the lines, and thus lead to substantial improvements at much lower cost, and much more quickly. In the analyses conducted thus far, it appears that the marker, all other things being equal, is associated with a significant improvement in milk production in the Carlin-M Ivanhoe Bell family.

Thus, the objects of the present invention include:

(a) providing an assay of the above kind for the presence of a genetic marker associated with improved milk production traits;

(b) providing a kit of the above kind to be used in connection with such assays;

(c) providing a breeding method of the above kind for using such assays;

(d) producing cattle by using breeding methods of the above kind; and (e) providing such assays, kits, and methods so as to save time and money.

These and still other objects and advantages of the present invention will be apparent from the description which follows. In this description, the preferred embodiments of the invention will be described with reference to the accompanying drawings. These embodiments do not represent the full scope of the invention. Rather, the invention may be employed in other embodiments. Reference should therefore be made to the claims to interpret the breadth of the invention.

DESCRIPTION OF THE PREFERRED EMBODIMENTS

Figure 1:
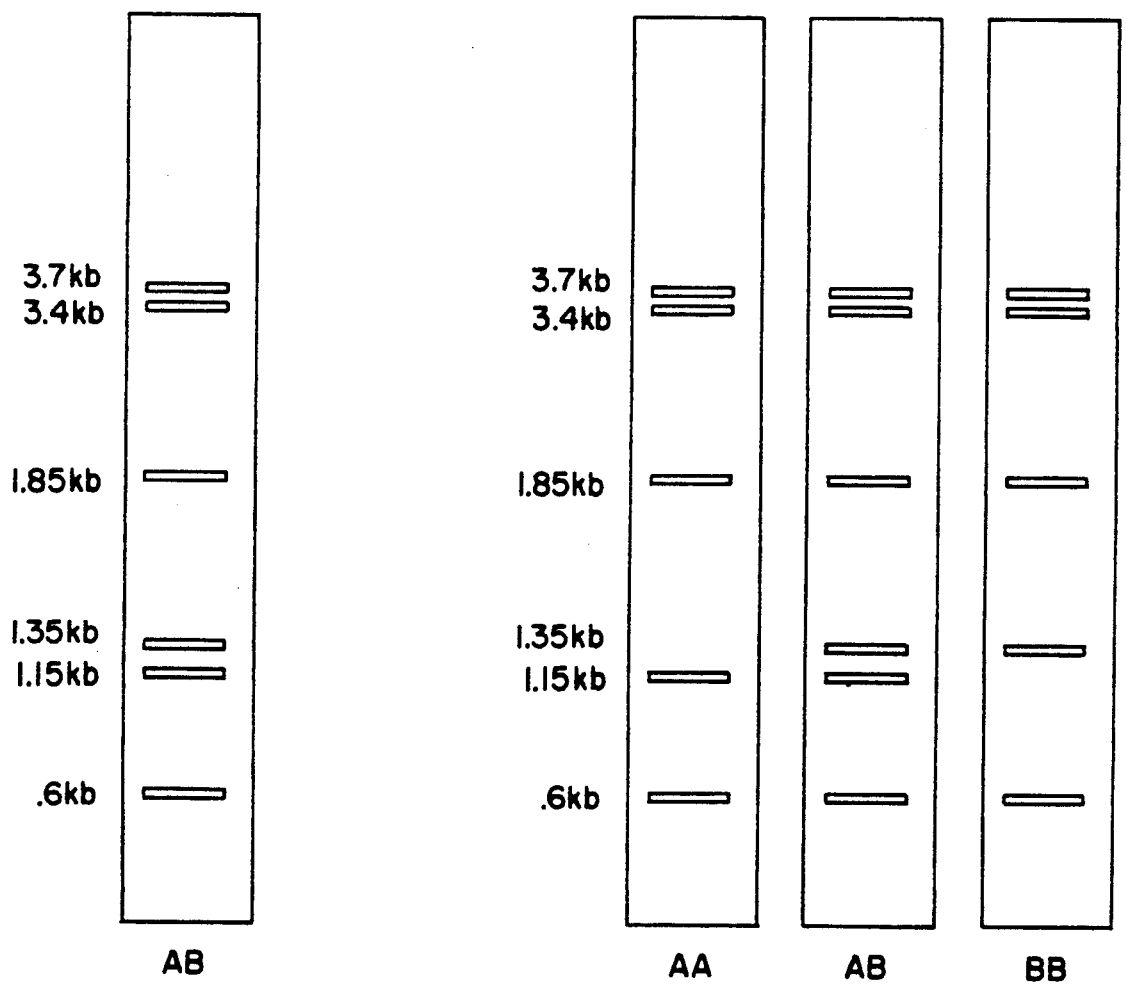
FIG. 1 depicts (in schematic form) hybridization patterns of a heterozygus sire and of three possible sons.

We followed the following general steps:

1. Extraction Of DNA: Semen from commercially available Holstein bulls (or other bovine cells) provided the source of the DNA to be tested. Spermatozoa were then treated so that their DNA would be released from the cell and concentrated in relatively pure form.

2. Digestion And Fragment Separation: A restriction enzyme (preferably Ava II) which recognizes a sequence in double stranded DNA near bovine prolactin was used to cleave the DNA. DNA fragments were separated by electrophoresis in agarose gels against standards of known size. The gels were stained with ethidium bromide and photographed. Fragments of DNA were transferred to nylon membranes.

3. Hybridization: Blots were hybridized in high stringency conditions to bovine prolactin cDNA that had been radio-labelled by nick-translation. Blots were washed with solutions of decreasing salt concentration to remove any nonspecifically bound probe. Blots bound to the labelled probe were exposed to autoradiography film with intensifying screens for three to five days at low temperature.

4. Correlation To Data On Milk Production Of Progeny: Three genotypes were discovered by analysis of hybridization patterns of a particular family of sons.

1. Extraction

Semen from commercially available registered U.S. Holstein progeny bulls of the Carlin-M Ivanhoe Bell family provided the source material from which genomic DNA was isolated. DNA was extracted from sperm using a procedure modified from E. Borenfreund et al., 297 Nature 1375-77 (1961). Briefly, frozen 0.5 ml artificial insemination units containing approximately $30 \times 10^6$ sperm/unit were allowed to thaw at room temperature. The thawed semen was then treated with 2-mercaptoethanol in 10 mM Tris, pH 8.0, 100 mM NaCl, 50 mM EDTA and 0.25% sodium dodecyl sulfate (SDS) and incubated at 53° to 55° C. for 30 minutes. Semen samples were cooled in an ice bath for 10 minutes prior to addition of proteinase K to a final concentration of 200 µg/ml and incubation continued at 37° C. for 3 hours. DNA was extracted sequentially with phenol followed by phenol:chloroform: isoamyl alcohol (25:24:1) and finally chloroform:isoamyl alcohol (24:1).

Following extraction, the DNA was precipitated with an equal volume of cold isopropanol (−20° C.). The DNA was removed by spooling it onto a polyethelene pipet tip and air dried before being dissolved in 10 mM Tris, pH 7.5, containing 1 mM EDTA and 50 mM NaCl.

Concentrations of DNA in each sample were estimated by their optical density at 260 nm. Samples were stored at 4° C.

2. DIGESTION/SEPARATION

Prior to enzymatic digestion of the DNA, 15 µg of isolated genomic DNA were dialyzed against a buffer compatible with the restriction endonuclease employed. The preferred restriction enzyme to digest the sperm genomic DNA from subsets of bulls was Ava II (New England BioLabs, Beverly, Massachusetts). DNA samples were digested in accordance with the enzyme manufacturer's standard recommendations for at least six hours.

The resulting DNA fragments were separated by electrophoresis in agarose gels (1.0% agarose) in 40 mM Tris, 20 mM NaCl, 20 mM acetic acid and 2 mM EDTA. After completion of electrophoresis, gels were stained with ethidium bromide (2 µg/ml) and photographed using UV light. Transfer to DNA to Hybond-N membrane (Amersham, Arlington Heights, Ill.) was accomplished using the manufacturer's recommended modified Southern blotting method. See generally E.M. Southern, 98 J. Mol. Biol. 503-517 (1975).

DNA fragments were crosslinked to the nylon membrane by baking for 2 hours at 80° C. followed by a two minute exposure to 300 NM UV light from a transilluninator (Fotodyne, New Berlin, Wis.).

3. Hybridization

Blots were preybridized on the membrane in 5x SSPE (0.9 M NaCl, 25 nM sodium phosphate, pH 7.4 and 2.5 mM EDTA) 0.4% SDS, 50% deionized formamide, 5x Denhardts (0.1% each of bovine serum albumin, Ficoll, and polyvinylpyrrolidone), and denatured herring sperm (50µg/ml) at 42° C. for 6 hours.

A plasmid containing a portion of bovine prolactin cDNA (pBPRL27) was radio-labelled by nick-translation. See e.g. P. Rigby et al., 113 J. Mol Biol. 237-251 (1977). pBPRL27 with the restriction endonuclease employed. The preferred restriction enzyme to digest the sperm genomic DNA from subsets of bulls was Ava II (New England BioLabs, Beverly, Mass.). DNA samples were digested in accordance with the enzyme manufacturer's standard recommendations for at least six hours.

The resulting DNA fragments were separated by electrophoresis in agarose gels (1.0% agarose) in 40 mM Tris, 20 mM NaCl, 20 mM acetic acid and 2 mM EDTA. After completion of electrophoresis, gels were stained with ethidium bromide (2 µg/ml) and photographed using UV light. Transfer to DNA to Hybond- N membrane (Amersham, Arlington Heights, Ill.) was accomplished using the manufacturer's recommended modified Southern blotting method. See generally E.M. Southern, 98 J. Mol. Biol. 503-517 (1975).

DNA fragments were crosslinked to the nylon membrane by baking for 2 hours at 80° C. followed by a two minute exposure to 300 NM UV light from a transilluninator (Fotodyne, New Berlin, Wis.).

3. Hybridization

Blots were prehubridized on the membrane in 5x SSPE (0.9 M NaCl, 25 nM sodium phosphate, pH 7.4 and 2.5 mM EDTA) 0.4% SDS, 50% deionized formamide, 5x Denhardts (0.1% each of bovine serum albumin, Ficoll, and polyvinylpyrrolidone), and denatured herring sperm (50μg/ml) at 42° C. for 6 hours.

A plasmid containing a portion of bovine prolactin cDNA (pBPRL27) was radio-labelled by nick-translation. See e.g. P. Rigby et al., 113 J. Mol Biol. 237-251 (1977). pBPRL27 is deposited with the American Type Culture Collection, Rockville, Md., as ATCC No. 40574. Samples from the deposit are available in accordance with U.S. patent law requirements upon issuance of the patent and the requirements of any applicable foreign patent laws. No patent license is intended by such availability. Another plasmid cDNA which could be used for this purpose is (pBPRL72) from N. L. Sasavage, et al. 257 J. Biol. Chem. 678-681 (1982).

The labelled probe was added with fresh hybridization solution and the incubation continued for 36 hours. Blots were washed twice with 2x SSC (300 mM NaCl and 30 mM Na citrate, pH 7.0) at 65° C. for 15 minutes, followed by 2x SSC and 0.1% SDS at 65° C. for 30 minutes. The final wash was at high stringency (0.1x SSC at 65° C. for 10 minutes). Blots were exposed to Kodak XAR-5 film with intensifying screens for 3 to 5 days at −80° C. The probe was removed according to the manufacturer's recommendations for multiple probing of blots.

4. Correlation Analysis

The resulting hybridization patterns were analyzed. Three types were identified. The patterns of these types (labelled AA, AB, and BB, respectively) are shown in FIG. 1 as possible offspring of type AB. Analysis of family lines shows that sons of the AA type all carry the A allele, and sons of the BB type are certain of not carrying the marker. Sons of the AB type would be a mixture of those carrying either the B from the sire or A from the sire.

A statistical model was then formulated to test for differences in predicted genetic values for milk production traits between those carrying A from the sire versus those carrying B from the sire. Results of the analysis revealed a statistically significant higher genetic transmitting value for milk yield from the sons in this family who carried the A marker.

FIG. 1 shows that the "most preferred" AA pattern shows fragments of about 1.15 kb, but not one at about 1.35. The second most preferred AB pattern has lines at 1.35 and 1.15. The 1.15 fragment is missing in the third (undesired) pattern.

Applicant has deposit a bovine sperm cell 14H9689 of type AB with the American Type Culture Collection, Rockville, Md., as ATCC No. 40573. Samples from the deposit are available in accordance with U.S. patent law requirements upon issuance of the patent and the requirements of any applicable foreign patent laws. No patent license is intended by such availability. It will be appreciated that one skilled in the art can use this "known" to confirm the location of the key fragments' hybridization pattern.

It should be understood that the above description deals with a preferred embodiment of the invention, and that many other embodiments are within the scope of the invention. For example, the invention should work with other types of bovine cells that contain DNA (other than just sperm). In this regard, it should be applicable to other cells types.

Also, while Ava II restriction fragments associated with prolactin have been chosen as a model system, other restriction enzymes when used with prolactin (or prolactin adjacent) probes may also yield characteristic hybridization patterns, that can be compared to knowns developed using the Ava II patterns. Moreover, while the primary utility of the invention is for Carlin-M Ivanhoe Bell progeny, the principles of the invention may also apply to other Holstein families.

Also, it should be noted that the presence of the marker is a statistical indication of improved production. Thus, breeders will also want to continue to use their standard breeding techniques when this marker is used. This marker does not replace such techniques. It supplements them.

We claim:

1. An assay for the presence in a bovine gene sequence of a genetic marker that is located within 1.5 kb of at least a part of a bovine prolactin coding gene in the sequence, the marker being located at least in part on a portion of the bovine gene sequence between two Ava II restriction enzyme sites that are both within 1.5 kb of said bovine prolactin coding gene, said marker being indicative of an inheritable trait of increased milk production in female progeny, said assay comprising:

(a) exposing the gene sequence to a restriction enzyme that cuts only at the same recognition sites as Ava II restriction enzyme so as to yield gene fragments of varying lengths;

(b) separating at least some of the fragments from others;

(c) hybridizing a plurality of probes that contain a portion of a bovine prolactin gene sequence to the separated fragments; and (d) then comparing the results of the hybridization with hybridization assay results for a bovine gene sequence known to have the marker or for a bovine gene sequence known not to have the marker.

2. The assay of claim 1, wherein the bovine gene sequence is from a Holstein bovine cell.

3. The assay of claim 2, wherein the bovine gene sequence is from a Carlin-M Ivanhoe Bell cell, or its progeny, or a cell derived from either.

4. The assay of claim 3, wherein the probe is a labelled cDNA probe.

5. The assay of claim 4, wherein the fragments are separated by electrophoresis.

6. A kit for assaying for the presence in a bovine gene sequence of a genetic marker that is located within 1.5 kb of at least a part of a bovine prolactin coding gene in the sequence, the marker being located at least in part on a portion of the bovine sequence between two Ava II restriction enzyme sites that are both located within 1.5 kb of said bovine prolactin coding gene, the marker being indicative of an inheritable trait of increased milk production in female progeny, said kit comprising:

a bovine gene sequence known to have the marker; and a probe containing a portion of a bovine prolactin gene sequence capable of hybridizing to an Ava II restriction fragment of said bovine gene sequence that is known to have the marker.

7. The kit of claim 6, wherein the probe is a cDNA sequence of a portion of bovine prolactin.

8. The kit of claim 7, wherein the probe is a radio-labelled cDNA of bovine prolactin.

9. The kit of claim 6, wherein the bovine gene sequence known to have the marker is from ATCC 40573, or its progeny, or gene sequences derived from either.

10. The kit of claim 6, wherein the kit further comprises the restriction enzyme Ava II.

11. An assay for the presence in a bovine gene sequence of a genetic marker indicative of an inheritable trait of increased milk production in female progeny, said assay comprising:

(a) exposing the gene sequence to a restriction enzyme that cuts only at the same recognition sites as Ava II restriction enzyme so as to yield gene fragments of varying lengths;

(b) separating at least some of the fragments from others;

(c) hybridizing a plurality of probes that contain a portion of a bovine prolactin gene sequence to the separated fragments; and (d) then comparing the results of the hybridization with hybridization assay results for a bovine gene sequence known to have the marker or for a bovine gene sequence known not to have the marker.

* * * * *